US012751947B2

(12) United States Patent
Umrethia et al.

(10) Patent No.: US 12,751,947 B2
(45) Date of Patent: Oct. 6, 2026

(54) ORAL LIQUID FORMULATION OF APIXABAN

(71) Applicant: Liqmeds Worldwide Limited, Weedon (GB)

(72) Inventors: Manish Umrethia, Ahmedabad (IN); Chintan Pansara, Ahmedabad (IN)

(73) Assignee: LIQMEDS WORLDWIDE LIMITED, Weedon (GB)

( * ) Notice: Subject to any disclaimer, the term of this patent is extended or adjusted under 35 U.S.C. 154(b) by 3 days.

(21) Appl. No.: 19/044,129

(22) Filed: Feb. 3, 2025

(65) Prior Publication Data

US 2025/0177369 A1 Jun. 5, 2025

Related U.S. Application Data

(63) Continuation-in-part of application No. PCT/IB2024/057385, filed on Jul. 31, 2024.

(30) Foreign Application Priority Data

Aug. 1, 2023 (IN) ............................. 202321051585

(51) Int. Cl.

| | |
|---|---|
| ***A01N 43/00*** | (2006.01) |
| ***A01N 43/46*** | (2006.01) |
| ***A61K 9/00*** | (2006.01) |
| ***A61K 9/08*** | (2006.01) |
| ***A61K 31/4545*** | (2006.01) |
| ***A61K 31/55*** | (2006.01) |
| ***A61K 47/10*** | (2017.01) |
| ***A61K 47/12*** | (2006.01) |
| ***A61K 47/36*** | (2006.01) |

(52) U.S. Cl.

CPC ........ *A61K 31/4545* (2013.01); *A61K 9/0053* (2013.01); *A61K 9/08* (2013.01); *A61K 47/10* (2013.01); *A61K 47/12* (2013.01); *A61K 47/36* (2013.01)

(58) Field of Classification Search

None

See application file for complete search history.

(56) References Cited

FOREIGN PATENT DOCUMENTS

| | | | |
|---|---|---|---|
| CN | 113384526 | A1 | 9/2021 |
| EP | 4450064 | A1 | 10/2024 |
| WO | 2023/012610 | A1 | 2/2023 |
| WO | 2023/072967 | A1 | 5/2023 |
| WO | 2023/218482 | A1 | 11/2023 |

OTHER PUBLICATIONS

Wang CC et al., Design and evaluation of oral formulation for apixaban, Heliyon, vol. 9, No. 8, availableonline Jul. 19, 2023 , https://doi.org/10.1016/j.heliyon.2023.e18422 (Year: 2023).*

ELIQUIS® (Apixaban) Tablet, Prescribing Information, Bristol-Myers Squibb Company, Apr. 2021, 41 pp.

Caraballo ML et al. "Compounded Apixaban Suspensions for Enteral Feeding Tubes", Hospital Pharmacy, vol. 52(7):478-482 (2017).

* cited by examiner

*Primary Examiner* — Layla Soroush

(74) *Attorney, Agent, or Firm* — Merchant & Gould P.C.; Daniel R. Evans; Daniel J. Pereira

(57) ABSTRACT

Disclosed herein relates to an oral liquid formulation of apixaban and more specifically an oral liquid formulation of apixaban comprising a therapeutically effective amount of apixaban, a salt or prodrug thereof; one or more viscosifying agents; one or more buffering agents to provide a formulation pH of from about 3.5 to about 4.5, and one or more pharmaceutically acceptable excipients. Also disclosed herein relates to a process for preparing an oral liquid formulation of apixaban and a method of using the same.

21 Claims, No Drawings

ORAL LIQUID FORMULATION OF APIXABAN

RELATED APPLICATIONS

This application is a continuation-in-part of International Application No. PCT/IB2024/057385, filed on Jul. 31, 2024, which claims priority to Indian Patent Application number 202321051585, filed on Aug. 1, 2023, the subject matter of which is incorporated by reference.

FIELD

Disclosed herein is an oral liquid formulation of apixaban and more specifically, disclosed herein relates to an oral liquid formulation of apixaban which is comprising a therapeutically effective amount of apixaban, a salt or prodrug thereof; one or more viscosifying agents; one or more buffering agents to provide a formulation pH of from about 3.5 to about 4.5, and one or more pharmaceutically acceptable excipients. Also disclosed herein related to a process of preparation of an oral liquid formulation of apixaban and a method of using the same.

BACKGROUND

Atrial fibrillation (AFib or AF) is an abnormal heart rhythm (arrhythmia) characterized by rapid and irregular beating of the atrial chambers of the heart. An arrhythmia is when the heart beats too slowly, too fast, or in an irregular way. When a person has AFib, the normal beating in the upper chambers of the heart (the two atria) is irregular, and blood does not flow as well as it should from the atria to the lower chambers of the heart (the two ventricles). AFib may happen in brief episodes, or it may be a permanent condition. Some of the symptoms are: irregular heartbeat, heart palpitations, light-headedness, extreme fatigue, shortness of breath and chest pain.

Apixaban, sold under the brand name ELIQUIS, is an anticoagulant medication used to treat and prevent blood clots and to prevent stroke in people with or without nonvalvular atrial fibrillation through directly inhibiting factor Xa. Also, it can be used to lower the risk of stroke and embolism in people with non-valvular atrial fibrillation.

Apixaban is a highly selective, orally bioavailable, and reversible direct inhibitor of free and clot-bound factor Xa. Factor Xa catalyzes the conversion of prothrombin to thrombin, the final enzyme in the coagulation cascade that is responsible for fibrin clot formation. Apixaban has no direct effect on platelet aggregation, but by inhibiting factor Xa, it indirectly decreases clot formation induced by thrombin.

Drug absorption is a pharmacokinetic parameter that refers to the way a drug is absorbed from a pharmaceutical formulation into the bloodstream. Several factors can affect the absorption of a drug into the body. These include:

Physicochemical properties (e.g. solubility)

Drug formulation (e.g. tablets, capsules, solutions)

The route of administration (e.g. oral, buccal, sublingual, rectal, parenteral, topical, or inhaled)

The rate of gastric emptying.

Currently, tablet and capsule formulation drugs are highly available in the market. But the absorption of these formulations take time when compared with the liquid formulations. The tablets and capsule takes time for absorption as they first need to be dissolve and disintegrate and then gets absorbed. Thus, there is always a need to develop formulations that can easily administered and can get easily absorbed. Liquid formulations generally overcome the drawbacks of solid and tablet formulations.

Aiming at the problem of low bioavailability of apixaban, the disclosed apixaban formulation may improve the solubility and dissolution rate of apixaban, increase the permeability of apixaban, and be conductive to improving the oral absorption characteristic of the apixaban and improve the bioavailability of the medicament.

Thus, the inventors of the formulation disclosed herein have developed an oral liquid formulation of apixaban with aims to overcome problems cited above by preparing an oral liquid formulation of apixaban.

Objectives

The main objective disclosed herein relates to an oral liquid formulation of apixaban, a salt or prodrug thereof.

Another objective provides an oral liquid formulation of apixaban, a salt or prodrug thereof which is stable.

Yet another objective provides an oral liquid formulation of apixaban, a salt or prodrug thereof which provides better patient compliance.

Yet another objective provides an oral liquid formulation of apixaban, a salt or prodrug thereof which is easy to manufacture at large scale.

Yet another objective provides an oral liquid formulation of apixaban, a salt or prodrug thereof which gives faster absorption and quicker onset of action.

SUMMARY

The formulation disclosed herein relates to an oral liquid formulation of apixaban.

The main aspect disclosed herein provides an oral liquid formulation of apixaban, a salt or prodrug thereof.

The main aspect disclosed herein provides an oral liquid formulation of apixaban comprising a therapeutically effective amount of apixaban, a salt or prodrug thereof; one or more viscosifying agents; one or more buffering agents to provide a formulation pH of from about 3.5 to about 4.5, and one or more pharmaceutically acceptable excipients.

Another aspect disclosed herein provides an oral liquid formulation of apixaban consisting of a therapeutically effective amount of apixaban, a salt or prodrug thereof; one or more viscosifying agents; one or more buffering agents to provide a formulation pH of from about 3.5 to about 4.5, and one or more pharmaceutically acceptable excipients.

Another aspect disclosed herein provides a process for the preparation of an oral liquid formulation of apixaban.

One more aspect disclosed herein provides an oral liquid formulation of apixaban, a salt or prodrug thereof to reduce the risk of stroke and systemic embolism in patients with non-valvular atrial fibrillation and deep vein thrombosis and pulmonary embolism.

One more aspect disclosed herein provides an oral liquid formulation of apixaban, a salt or prodrug thereof for use as a medicament for the treatment to reduce the risk of stroke and systemic embolism in patients with non-valvular atrial fibrillation and deep vein thrombosis and pulmonary embolism.

DETAILED DESCRIPTION

The main embodiment disclosed herein relates to an oral liquid formulation of apixaban, a salt or prodrug thereof.

The detailed description set forth below is intended as a description of exemplary embodiments and is not intended to represent the only forms in which the exemplary embodiments may be constructed and/or utilized. The description sets forth the functions and the sequence of steps for constructing and/or operating the exemplary embodiments. However, it is to be understood that the same or equivalent functions and sequences which may be accomplished by different exemplary methods are also intended to be encompassed within the spirit and scope of the invention.

As defined herein, all scientific and technical terms used herein have the same meaning as commonly understood by one of ordinary skill with respect to pharmaceutical sciences.

Although any process and materials similar or equivalent to those described herein can be used in the practice or testing formulations disclosed herein, the specific methods and materials are now described.

The singular forms "a," "an" and "the" specifically also encompass the plural forms of the terms to which they refer, unless the content clearly dictates otherwise. The expressions "about" is used herein to means approximately, in the region of, roughly, or around.

As stated herein, the expressions "comprise(s)" and "comprising" have their customary meanings. When used in the context of a process, the term "comprising" means that the process includes at least the recited steps, but may include additional steps. When used in the context of a composition, the term "comprising" means that the composition includes at least the recited features or components, but may also include additional features or components. One will understand that the expression "consisting of" may replace the expression "comprising" for a claimed formulation, process, or method. One will further understand that the expression "consisting essentially of" may replace the expression "comprising" for a claimed formulation, process or method.

The following terms are used interchangeably herein: "active", "drug", and "active ingredient".

A "therapeutically effective amount" or "effective amount" is that amount of a pharmaceutical agent to achieve a pharmacological effect. The term "therapeutically effective amount" includes, for example, a prophylactically effective amount.

As used herein the word "liquid formulation" refers to liquid oral formulation like solution, suspension or emulsion, more specifically in the form of suspension.

The expressions "about" is used synonymously with the term "approximately." As one of ordinary skill would understand, the exact boundary of "about" will depend on the component of the composition. Illustratively, the use of the term "about" indicates that values slightly outside the cited values, i.e., plus or minus 0.1% to 10%, which are also effective and safe. Thus, compositions slightly outside the cited ranges are also encompassed by the scope of the present claims.

The expressions "pH", as used herein, is meant "apparent pH" wherein the pH measurement is carried out on the apixaban containing composition in final form, for example, by measuring the pH of the formulation.

The main embodiment disclosed herein provides an oral liquid formulation of apixaban comprising a therapeutically effective amount of apixaban, a salt or prodrug thereof; one or more viscosifying agents; one or more buffering agents to provide a formulation pH of from about 3.5 to about 4.5, and one or more pharmaceutically acceptable excipients.

Another aspect disclosed herein provides an oral liquid formulation of apixaban consisting of a therapeutically effective amount of apixaban, a salt or prodrug thereof; one or more viscosifying agents; one or more buffering agents to provide a formulation pH of from about 3.5 to about 4.5, and one or more pharmaceutically acceptable excipients.

As per one embodiment disclosed herein, apixaban, a salt or prodrug thereof can be present in the formulation in an amount of from about 0.5 mg/mL to about 500 mg/mL, an all values in between, such as, from about 1 mg/mL to about 200 mg/mL, from about 1 mg/mL to about 150 mg/mL, from about 1 mg/mL to about 100 mg/mL, from about 1 mg/mL to about 50 mg/mL, from about 1 mg/mL to about 40 mg/mL, from about 1 mg/mL to about 30 mg/mL, from about 1 mg/mL to about 10 mg/mL, about 1 mg/mL, or 1 mg/mL.

The formulation disclosed comprises particulate apixaban having a particle size distribution of NMT 5 microns (D10), NMT 10 microns (D50), and between about 10 microns to about 60 microns (D90), including a D90 between about 10 microns to about 30 microns and all values in between, such as 12 microns, 14 microns, 16 microns, 18 microns, 20 microns, 22 microns, 24 microns, 26 microns, 28 microns, 30 microns, 32 microns, 34 microns, 36 microns, 38 microns, 40 microns, 42 microns, 44 microns, 46 microns, 48 microns, 50 microns, 52 microns, 54 microns, 56 microns, and 58 microns.

In one aspect, apixaban is the only active pharmaceutical ingredient in the formulation.

In another aspect, the formulation disclosed herein has a viscosity (Spindle No. 62@50 rpm) of about 400 cP to about 700 cP and all values in between, such as 420 cP, 440 cP, 460 cP, 480 cP, 500 cP, 520 cP, 540 cP, 560 cP, 580 cP, 600 cP, 620 cP, 640 cP, 660 cP, and 680 cP. In one aspect, the formulation disclosed herein as a viscosity (Spindle No. 62 @ 50 rpm) after storage at 25±2° C. and 60±5% RH of about 440 cP to about 540 cP, including all values in between such as 460 cP, 480 cP, 500 cP, and 520 cP.

A further aspect relates to a ready-to-use liquid formulation comprising apixaban in an amount of about 1 mg/mL; one or more pharmaceutically acceptable excipients; a vehicle comprising glycerin and water and a means for providing a formulation viscosity of from 400 cP to 700 cP (including all values in between).

Yet a further aspect relates to a ready-to-use liquid formulation comprising apixaban in an amount of about 1 mg/mL and having a D90 particle size of between about 10 microns to about 60 microns (and all values in between); one or more pharmaceutically acceptable excipients; a vehicle comprising glycerin and water and a means for providing a formulation viscosity of from 400 cP to 700 cP (including all values in between).

As per another embodiment, one or more viscosifying agents can be selected from methyl cellulose, bentonite, hectorite, magnesium aluminum silicate, microcrystalline cellulose, xanthan gum, acacia, tragacanth, guar gum, colloidal silicon dioxide, liquid sorbitol, liquid maltitol, sucrose, fructose, dextrose, maltodextrin and polydextrose, or any combination thereof.

As per one aspect, the viscosifying agent is liquid sorbitol. In another aspect, the viscosifying agent comprises liquid sorbitol comprising about 70% w/v sorbitol and about 30% w/v water.

As per one embodiment, one or more viscosifying agents can be used in the range of from about 10 mg/mL-about 500 mg/mL, and all values in between, such as from about 50 mg/mL-about 500 mg/mL, from about 100 mg/mL-about 500 mg/mL, from about 100 mg/mL-about 300 mg/mL, as well as for example, about 20 mg/mL, about 50 mg/mL, about 100 mg/mL, about 200 mg/mL, about 300 mg/mL, about 400 mg/mL, and about 450 mg/mL.

The buffers used in the formulation disclosed herein are generally recognized as safe (GRAS) by the U.S. Food and Drug Administration.

As per one embodiment, one or more buffering agents can be selected from citrate, aconitate, formate, glutarate, glutamate, succinate, sulfamate, tris, glycinate, and salts or acids thereof, and any combination thereof. A specifically contemplated buffer is comprised of citric acid, monobasic citrate, dibasic citrate, and tribasic citrate, in which the mono-, di-, or tribasic citrate forms have associated counterions and thus, may collectively be referred to as citrate salts (e.g., citrate buffer). The associated counterions include, for example, sodium, potassium, ammonium, calcium, etc. For instance, a particular citrate salt contemplated herein is sodium citrate, which may exist as an anhydrous form, hydrated form, such as, a dihydrate or a pentahydrate.

As per one aspect, citrate (i.e., citric acid and sodium citrate) is used as or consists of the one or more buffering agents.

As per one embodiment, one or more buffering agents used in the range of from about 0.5 mg/mL-about 50 mg/mL and all values in between, such as, from about 0.5 mg/mL-about 30 mg/mL, from about 1 mg/mL-about 30 mg/mL, or from about 1 mg/mL-about 20 mg/mL, as well as for example, about 1 mg/mL, about 5 mg/mL, about 10 mg/mL, about 10.50 mg/mL, about 12.25 mg/mL, about 15 mg/mL, about 20 mg/mL, about 22.75 mg/mL, about 30 mg/mL, about 40 mg/mL, and about 45 mg/mL.

In one aspect, the weight ratio of citric acid anhydrous to tri-sodium citrate dihydrate in the oral liquid formulation disclosed herein is about 1.17:1.

As per another embodiment, one or more pharmaceutically acceptable excipients comprises antifoaming agent, thickening agent, a humectant, a sweetening agent, a preservative, a flavouring agent, or a combination thereof.

As per one embodiment, one or more antifoaming agents can be selected from simethicone, sodium tetradecyl sulfate, dodecyl sulfate, poloxamers, sorbitan monolaurate, and lauryl glucoside, or any combination thereof.

As per one aspect, simethicone is used as antifoaming agent.

As per one embodiment, one or more antifoaming agents used in the range of from about 0.5 mg/mL-about 20 mg/mL and all values in between, such as, from about 0.5 mg/mL-about 15 mg/mL, from about 1 mg/mL-about 15 mg/mL, and from about 1 mg/mL-about 10 mg/mL, as well as, for example, about 1 mg/mL, about 2 mg/mL, about 3 mg/mL, about 4 mg/mL, about 5 mg/mL, about 10 mg/mL, about 15 mg/mL, and about 19 mg/mL.

In one aspect, the weight ratio of apixaban to sorbitol to simethicone to glycerin in the oral liquid formulation disclosed herein is about 1:200:0.333:200.

As per one embodiment, one or more thickening agents can be selected from methyl cellulose, bentonite, hectorite, magnesium aluminum silicate, microcrystalline cellulose, xanthan gum, acacia, tragacanth, guar gum and colloidal silicon dioxide, or any combination thereof.

As per one aspect, xanthan gum is used as thickening agent.

In one aspect, the weight ratio of apixaban to xanthan gum in the oral liquid formulation disclosed herein is about 0.22:1, or 22:100.

As per on embodiment of the present invention, one or more thickening agents used in the range of from about 0.5 mg/mL-about 20 mg/mL, and all values in between, such as, from about 0.5 mg/mL-about 15 mg/mL, from about 1 mg/mL-about 15 mg/mL, and from about 1 mg/mL-about 10 mg/mL, as well as, for example, about 1 mg/mL, about 2 mg/mL, about 3 mg/mL, about 4 mg/mL, about 4.5 mg/mL, about 5 mg/mL, about 10 mg/mL, about 15 mg/mL, and about 19 mg/mL.

As per one embodiment, one or more humectants can be selected from glycerin, hyaluronic acid, salicylic acid, alpha hydroxy acids (AHAs), such as glycolic acid, propylene glycol, honey, and sorbitol, or any combination thereof.

As per one aspect, glycerin is used as humectant, thickening agent, and a vehicle.

As per one embodiment, glycerin (or the humectant) is used in the range of from about 1 mg/mL-about 500 mg/mL and all values in between, such as, from about 1 mg/mL-about 400 mg/mL, from about 1 mg/mL-about 300 mg/mL, and from about 1 mg/mL-about 250 mg/mL, as well as, for example, about 2 mg/mL, about 5 mg/mL, about 10 mg/mL, about 20 mg/mL, about 50 mg/mL, about 100 mg/mL, about 200 mg/mL, about 300 mg/mL, about 400 mg/mL, and about 450 mg/mL.

As per one embodiment, one or more sweetening agents can be selected from but not limited to glucose, sucralose, trehalose, fructose, xylose, dextrose, galactose, tagatose, maltose, sucrose, glycerol, dulcitol, mannitol, lactitol, sorbitol, cyclamate or the corresponding sodium or calcium salt, or acesulfame or the potassium salt thereof, ammonium glycyrrhizinate, alitame, inulin, isomalt, neohesperidin dihydrochalcone, thaumatin and the like or any combination thereof.

As per one aspect, sucralose is used as sweetening agent.

As per one embodiment, sucralose or the sweetening agent can be used in the range of from about 0.1 mg/mL-about 20 mg/mL and all values in between, such as, from about 0.1 mg/mL-about 10 mg/mL, from about 0.5 mg/mL-about 10 mg/mL, and from about 0.5 mg/mL-about 5 mg/mL, such as, for example, about 0.2 mg/mL, about 0.5 mg/mL, about 1 mg/mL, about 2 mg/mL, about 3 mg/mL, about 4 mg/mL, about 5 mg/mL, about 10 mg/mL, about 15 mg/mL, and about 19 mg/mL.

As per one embodiment, one or more preservatives can be selected from but not limited to benzoic acid, potassium sorbate, sodium benzoate, chlorobutanol, benzalkonium chloride, benzethonium chloride, benzyl alcohol, chlorobutanol, m-cresol, myristyl gamma picolinium chloride, phenol, 2-phenoxyethanol, phenyl mercuric nitrate, phenyl ethyl alcohol, or any combination thereof.

As per one aspect, sodium benzoate is used as preservative.

As per one embodiment, sodium benzoate (or the preservative) can be used in the range of from about 0.01 mg/mL-about 10 mg/mL and all values in between, such as, from about 0.01 mg/mL-about 8 mg/mL, from about 0.05 mg/mL-about 5 mg/mL, and from about 0.05 mg/mL-about 3 mg/mL, such as, for example, about 0.02 mg/mL, about 0.05 mg/mL, about 0.1 mg/mL, about 0.5 mg/mL, about 1 mg/mL, about 2 mg/mL, about 4 mg/mL, about 6 mg/mL, about 8 mg/mL, and about 9 mg/mL.

As per one embodiment, one or more flavouring agents can be selected from but not limited to citrus oil, including lemon, lime and fruit essences, including apple, pear, peach, raspberry, cherry, plums pineapple, apricot, peppermint, frozen peppermint, tutti-frutti flavour and so forth and the like or any combination thereof.

As per one aspect, frozen peppermint flavour is used as flavouring agent.

As per one embodiment, one or more flavouring agents can be used in the range of from about 0.01 mg/mL-about 1 mg/mL and all values in between, such as, from about 0.05 mg/mL-about 1 mg/mL, from about 0.05 mg/mL-about 0.8 mg/mL, and from about 0.05 mg/mL-about 0.5 mg/mL, such as, for example, about 0.02 mg/mL, about 0.05 mg/mL, about 0.1 mg/mL, about 0.5 mg/mL, and about 0.9 mg/mL.

Vehicle can be considered as any inert substance, or mixture of substances, added to increase the volume of the liquid composition to make the liquid formulation disclosed herein in a suitable form.

As per one embodiment, the vehicle can be selected from purified water, glycerin, propylene glycol, glycerin containing buffers, polyethylene glycol, and polyethylene glycol 400, or any combination thereof.

As per preferred embodiment, a combination of glycerin and purified water is used as vehicle.

As per one embodiment, glycerin (or the vehicle) can be used in the range of from about 1 mg/mL-about 500 mg/mL and all values in between, such as, from about 1 mg/mL-about 400 mg/mL, from about 1 mg/mL-about 300 mg/mL, and from about 1 mg/mL-about 250 mg/mL, as well as, for example, about 2 mg/mL, about 5 mg/mL, about 10 mg/mL, about 20 mg/mL, about 50 mg/mL, about 100 mg/mL, about 200 mg/mL, about 300 mg/mL, about 400 mg/mL, and about 450 mg/mL.

In yet another aspect, the water can be used in the range of from about 400 mg/mL to about 800 mg/mL and all values in between, such as, 420 mg/mL, 440 mg/mL, 460 mg/mL, 480 mg/mL, 500 mg/mL, 520 mg/mL, 540 mg/mL, 560 mg/mL, 580 mg/mL, 600 mg/mL, 620 mg/mL, 640 mg/mL, 660 mg/mL, 680 mg/mL, 700 mg/mL, 720 mg/mL, 740 mg/mL, 760 mg/mL, and 780 mg/mL.

In one aspect, the weight ratio of apixaban to glycerin in the oral liquid formulation disclosed herein is about 0.005:1, or 1:200.

In one aspect, the oral liquid formulation disclosed herein does not include a sweetener (for example, saccharin sodium, xylitol, aspartame, etc.), a thickener (for example, hydroxy ethyl cellulose, sodium alginate, etc.), a preservative (for example, an alkyl ester of p-hydroxybenzoic acid which includes methyl paraben, propyl paraben, ethyl paraben, butyl paraben etc.), a dispersant (for example, polysorbate 80), an antioxidant (for example, sodium metabisulfite, ascorbic acid, butylated hydroxy anisole, butylated hydroxy toluene, vitamin E, vitamin E PEG 1000 succinate), a chelating agent (for example, EDTA), flavour (for example, vanilla, orange, strawberry, blueberry, grape, banana flavours, etc.), a solubilizer (for example, diethylene glycol monoethyl ether, caprylic capric polyethylene glycol glyceride, 15-hydroxystearic acid polyethylene glycol ester, etc.), pH regulator or buffer (for example, one or more of phosphoric acid and phosphate thereof, acetic acid and acetate thereof, lactic acid and lactate thereof, carbonic acid and carbonate thereof, boric acid and borate thereof, malic acid, tartaric acid, sodium hydroxide and potassium hydroxide, etc.), vehicle (for example, polyoxyl 35 castor oil, ethanol, macrogol-15-hydroxystearate, polyoxyl 15 hydroxystearate, etc.), hydrophilic polymers (for example, povidone, PVPK 12, povidone K30, copovidone, hydroxypropyl cellulose, hydroxypropyl methylcellulose, etc.), a surfactant (for example, sodium lauryl sulfate, docusate sodium, etc.), a suspending agent (for example, sodium carboxymethylcellulose).

As per one embodiment, purified water can be used to adjust the final volume of the formulation.

In one aspect, the weight ratio of apixaban to glycerin to purified water in the oral liquid formulation disclosed herein is about 1:200:1090.

As per one embodiment, the process of preparation of an oral liquid formulation of apixaban comprises:

Mixing together a therapeutically effective amount of apixaban, a salt or prodrug thereof; one or more viscosifying agents; one or more buffering agents to provide a pH of from about 3.5 to about 4.5, and one or more pharmaceutically acceptable excipients.

The process may further comprise dissolving the one or more buffering agents in purified water before adding the same to the formulation;

The process may further comprise adding a preservative, a sweetening agent, a humectant and an antifoaming agent;

The process may further comprise adding one or more thickening agents;

The process may further comprise adding one or more flavouring agents;

The process may further comprise mixing the formulation using a magnetic stirrer, and mixing at 500-1000 rpm, 4000-6000 rpm, or 500-6000 rpm; The process may further comprise the formulation in a HDPE Bottle.

As per another main embodiment, the process of preparation of an oral liquid formulation of apixaban comprises:

a) Dissolving buffering agent in purified water;
b) Adding preservative, sweetening agent, humectant, antifoaming agent in solution of step (a) and mixing with magnetic stirrer at 500 to 1000 rpm;
c) Adding Apixaban in step (b) and mixing with magnetic stirrer at 4000-6000 rpm;
d) Adding thickening agent in vessel containing vehicle and mixing with magnetic stirrer at 500 to 1000 rpm;
e) Adding solution of step (d) into solution of step (c) and mixing with magnetic stirrer at 1000-1200 rpm;
f) Adding viscosifying agent and flavouring agent in solution of step (e) and mixing with magnetic stirrer at 1000-1200 rpm;
g) Adjusting the volume with purified water and mixing with magnetic stirrer at 5500-6500 rpm till getting uniform formulation;
h) Storing the final formulation of step (g) High Density Polyethylene (HDPE) Bottle.

As per one embodiment, the liquid formulation can be selected from a solution or a suspension. In one aspect, the liquid formulation is in the form of a suspension.

As per one embodiment, an oral liquid formulation of apixaban, a salt or prodrug thereof is stable and provides better patient compliance.

As per one embodiment, the oral liquid formulation of apixaban, a salt or prodrug thereof used to reduce the risk of stroke and systemic embolism in patients with non-valvular atrial fibrillation and deep vein thrombosis and pulmonary embolism. One aspect is directed to a method to reduce the risk of stroke and systemic embolism in a patient with nonvalvular atrial fibrillation, which comprises administering to the patient in need thereof, a therapeutically effective amount of a formulation disclosed herein. For instance, a patient may consume orally about 5 mg of apixaban twice daily. In another aspect, a patient may consume orally about 2.5 mg of apixaban twice daily having two or more of the following characteristics: (1) age≥80 year, (2) body weight≤60 kg, and (3) a serum creatine of ≥1.5 mg/dL.

As per one embodiment, the patient is a human patient.

The formulation disclosed herein is further illustrated by the following examples which are provided to be exemplary and do not limit the scope of the subject matter claimed herein. While the formulation disclosed herein has been described in terms of its specific embodiments, certain modifications and equivalents will be apparent to those skilled in the art and are intended to be included within the scope of the formulation claimed herein.

EXAMPLES

Example 1. Vehicle Screening

For the selection of vehicle apixaban was dissolved in different vehicles like purified water alone or in combination with glycerin, propylene glycol, and polyethylene glycol (PEG) 400.

TABLE 1

| Batches for selection of Vehicle | | | | |
|---|---|---|---|---|
| | APXL/170621/1001A | APXL/170621/1001B | APXL/170621/1001C | APXL/170621/1001D |
| Ingredients | Quantity (mg/mL) | | | |
| Apixaban | 1.00 | 1.00 | 1.00 | 1.00 |
| Purified Water | 999.00 (Q.S. to 1 mL) | 504.00 (Q.S. to 1 mL) | 583.00 (Q.S. to 1 mL) | 547.00 (Q.S. to 1 mL) |
| Glycerin | — | 495.00 | — | — |
| Propylene glycol | — | — | 416.00 | — |
| PEG 400 | — | — | — | 452.00 |

TABLE 2

Result of batches for selection of Vehicle

| Batch No. | Time Point | Single Maximum Unknown impurity | Total Impurities | H-AXBRC02 | H-AXBRC01 |
|---|---|---|---|---|---|
| APXL/170621/1001 A | 60° C., 7 days | BQL | 0.25% | BQL (0.01%) | BQL (0.02%) |
| APXL/170621/1001 B | 60° C., 7 days | BQL | 0.42% | BQL (0.01%) | BQL (0.02%) |
| APXL/170621/1001 C | 60° C., 7 days | BQL | 0.26% | BQL (0.01%) | ND |
| APXL/170621/1001 D | 60° C., 7 days | 0.13% (RRT-0.77) | 0.78% | BQL (0.09%) | BQL (0.02%) |

BQL: Below Quantitation Limit; RRT: Relative Retention Time; ND: Not Detected.

Based on above data it can be concluded that only water or combination of water with glycerin and propylene glycol indicates less impurities as compared to batch with combination of water with polyethylene glycol 400. Glycerin is well accepted vehicle in liquid oral. Therefore, water and its combination with glycerin is finalized to be used as a vehicle for initial product development.

Example 2. Buffering Agent Screening

For the selection of buffering agent trial apixaban was dissolved in citrate buffer and phosphate buffer alone and in presence of glycerin, propylene glycol, and PEG 400.

TABLE 3

Batches for evaluating effect of buffer.

| Ingredients | APXL/170621/1002A | APXL/170621/1002B | APXL/170621/1002C | APXL/170621/1002D | APXL/170621/1003A | APXL/170621/1003B | APXL/170621/1003C | APXL/170621/1003D |
|---|---|---|---|---|---|---|---|---|
| | Quantity (mg/mL) | | | | | | | |
| Apixaban | 1.00 | 1.00 | 1.00 | 1.00 | 1.00 | 1.00 | 1.00 | 1.00 |
| 100 mM Citrate buffer pH 4 | 999.00 (Q.S. to 1 mL) | 495.00 (Q.S. to 1 mL) | 583.00 (Q.S. to 1 mL) | 547.00 (Q.S. to 1 mL) | — | — | — | — |
| 100 mM Phosphate buffer pH 7 | — | — | — | — | 999.00 (Q.S. to 1 mL) | 495.00 (Q.S. to 1 mL) | 583.00 (Q.S. to 1 mL) | 547.00 (Q.S. to 1 mL) |
| Glycerin | — | 504.00 | — | — | — | 504.00 | — | — |
| Propylene glycol | — | — | 416.00 | — | — | — | 416.00 | — |
| PEG 400 | — | — | — | 452.00 | — | — | — | 452.00 |

TABLE 4

Results for evaluating effect of buffer

| Batch No. | Time Point | Single Maximum Unknown Impurity | Total Impurities | H-AXBRC02 | H-AXBRC01 |
|---|---|---|---|---|---|
| APXL/170621/1002A | 60° C., 7 days | BQL | 0.37% | BQL (0.02%) | BQL (0.02%) |
| APXL/170621/1002B | 60° C., 7 days | BQL | 0.33% | BQL (0.01%) | BQL (0.02%) |
| APXL/170621/1002C | 60° C., 7 days | 0.12% (RRT-0.55) | 0.45% | BQL (0.02%) | BQL (0.02%) |
| APXL/170621/1002D | 60° C., 7 days | 0.13% (RRT-0.34) | 0.54% | BQL (0.02%) | BQL (0.02%) |
| APXL/170621/1003A | 60° C., 7 days | BQL | 0.23% | BQL (0.05%) | BQL (0.01%) |

TABLE 4-continued

Results for evaluating effect of buffer

| Batch No. | Time Point | Single Maximum Unknown Impurity | Total Impurities | H-AXBRC02 | H-AXBRC01 |
|---|---|---|---|---|---|
| APXL/170621/1003B | 60° C., 7 days | 0.28% (RRT-0.90) | 0.93% | 0.32% | BQL (0.01%) |
| APXL/170621/1003C | 60° C., 7 days | 0.12% (RRT-0.55) | 0.72% | 0.32% | BQL (0.00%) |
| APXL/170621/1003D | 60° C., 7 days | 0.28% (RRT-1.05) | 1.42% | 0.22% | BQL (0.01%) |

BQL: Below Quantitation Limit; RRT: Relative Retention Time

Based on above data it can be concluded that, in presence of glycerin and 100 mM citrate buffer in combination showed less impurities as compared to batches in combination with propylene glycol and polyethylene glycol 400. In presence of glycerin, propylene glycol or polyethylene glycol 400 in combination with 100 mM phosphate buffer showed relatively 10 higher but acceptable higher impurities. Therefore, glycerin with 100 mM citrate buffer was finalized to be used as a vehicle for initial product development.

Example 3. Two Formulation Batches Having Same Makeup (1021 and 1035) as Shown in Table 5

TABLE 5

Optimized formulation of oral liquid suspension of Apixaban

| Sr. No. | Ingredients | Quantity (mg) /mL |
|---|---|---|
| 1 | Apixaban | 1.00 |
| 2 | Sucralose | 2.00 |
| 3 | Xanthan gum | 4.50 |
| 4 | Sodium benzoate | 1.00 |
| 5 | Citric acid anhydrous | 12.25 |
| 6 | Sodium citrate | 10.50 |
| 7 | Simethicone | 3.00 |
| 8 | Liquid sorbitol | 200 |
| 9 | Frozen peppermint | 0.10 |
| 10 | Glycerine | 200 |
| 11 | Purified water | Q.S. to 1 mL |

Q.S.: Quantity Sufficient

Procedure:

a) The citric acid anhydrous and sodium citrate was dissolved in purified water;

b) The sodium benzoate, sucralose, glycerin, simethicone were added in solution of step (a) and mixed with magnetic stirrer at 500 to 1000 rpm;

c) Apixaban was added in step (b) and mixed with magnetic stirrer at 4000-6000 rpm;

d) The xanthan gum was added in vessel containing glycerin and mixed with magnetic stirrer at 500 to 1000 rpm;

e) The solution of step (d) was added into solution of step (c) and mixed with magnetic stirrer at 1000-1200 rpm;

f) The liquid sorbitol and frozen peppermint was added in solution of step (e) and mixed with magnetic stirrer at 1000-1200 rpm;

g) The volume was adjusted with purified water and mixed with magnetic stirrer at 5500-6500 rpm till getting uniform formulation;

h) Storing the final formulation of step (g) High Density Polyethylene (HDPE) Bottle.

Example 4. Thermal Stability Data for Final Optimized Formulation (1021 and 1035)

The thermal stability study was conducted for final formulation at accelerated stability condition 40° C.±2° C./NMT 75% RH and 25° C.±2° C./60±5% RH.

TABLE 6A

Results of stability study for Batch 1021

| | | | Batch No. 1021 (batch size 2500 mL) Packaging 185 CC HDPE bottle packed in secondary white box Temperature/Relative Humidity (% RH) | | | | | | |
|---|---|---|---|---|---|---|---|---|---|
| | | | 40° C. ± 2° C./NMT 75% RH | | | 25° C. ± 2° C./60 ± 5% RH | | | |
| Test Parameter | Storage Conditions | Initial | 1M Invert | 3M Invert | 6M Invert | 1M Invert | 3M Invert | 6M Invert | 12M Invert |
| Description | Off white-to-white suspension | Complies | Complies | Complies | Complies | Complies | Complies | Complies | Complies |
| Assay of Apixaban | 95.0% to 105.0% of labelled amount | 97.90% | 99.10% | 98.40% | 98.8% | 97.40% | 98.50% | 97.2% | 97.7% |

TABLE 6A-continued

Results of stability study for Batch 1021

| Test Parameter | Storage Conditions | Initial | Batch No. 1021 (batch size 2500 mL) Packaging 185 CC HDPE bottle packed in secondary white box Temperature/Relative Humidity (% RH) | | | | | | |
|---|---|---|---|---|---|---|---|---|---|
| | | | 40° C. ± 2° C./NMT 75% RH | | | 25° C. ± 2° C./60 ± 5% RH | | | |
| | | | 1M Invert | 3M Invert | 6M Invert | 1M Invert | 3M Invert | 6M Invert | 12M Invert |
| Assay of Sodium Benzoate | 80% to 110.0% of labelled amount | 97.20% | 98.70% | 97.60% | 97.7% | 97.10% | 98.00% | 96.8% | 97.1% |
| pH | Should be between 3.5 to 4.5 | 4.0 | 4.0 | 4.0 | 4.0 | 4.0 | 4.0 | 4.0 | 4.0 |
| Viscosity | AT 50 RPM, Spindle no.62, Should be between 400 cP to 700 cP | 484.2 cP | 468.6 cP | 449.4 cP | 448.8 cP | 481.8 cP | 481.2 cP | 466.2 cP | 453 cP |
| Related Substance (by HPLC) | | | | | | | | | |
| Impurity H-AXBRCO2 | NMT 0.5% | ND | ND | ND | ND | ND | ND | BQL | BQL |
| Impurity H-AXBRCO1 | NMT 0.5% | BQL | BQL | BQL | BQL | BQL | BQL | BQL | BQL |
| Single Max unknown Impurities | NMT 0.2% | BQL | BQL | BQL | BQL | BQL | BQL | 0.06 | 0.06 |
| Total Impurities | NMT 1.0% | 0.0 | 0.0 | 0.0 | 0.0 | 0.0 | 0.0 | 0.06 | 0.06 |

TABLE 6B

Results of stability study for Batch 1035

| Test Parameter | Storage Conditions | Initial | Batch No. 1035 (batch size 2500 mL) Packaging 185 CC HDPE bottle packed in secondary white box (fill volume 150 mL) Temperature/Relative Humidity (% RH) | | | |
|---|---|---|---|---|---|---|
| | | | 40° C. ± 2° C./NMT 75% RH | | 25° C. ± 2° C./60 ± 5% RH | |
| | | | 3M Invert | 6M Invert | 3M Invert | 6M Invert |
| Description | Off white-to-white suspension | Complies | Complies | Complies | Complies | Complies |
| Assay of Apixaban | 95.0% to 105.0% of labelled amount | 98.20% | 96.8% | 97% | 97% | 97% |
| Assay of Sodium Benzoate | 80% to 110.0% of labelled amount | 98.90% | 96.9% | 96.9% | 97.7% | 97.5% |
| pH | Should be between 3.5 to 4.5 | 3.93 | 4.03 | 4.03 | 4.01 | 4.02 |
| Viscosity | AT 50 RPM, Spindle no.62, Should be between 400 cP to 700 cP | 494.4 cP | 446.4 cP | 442.8 cP | 468.6 cP | 466.2 cP |

TABLE 6B-continued

Results of stability study for Batch 1035

| Test Parameter | Storage Conditions | Initial | Batch No. 1035 (batch size 2500 mL) Packaging 185 CC HDPE bottle packed in secondary white box (fill volume 150 mL) Temperature/Relative Humidity (% RH) 40° C. ± 2° C./NMT 75% RH 3M Invert | 40° C. ± 2° C./NMT 75% RH 6M Invert | 25° C. ± 2° C./60 ± 5% RH 3M Invert | 25° C. ± 2° C./60 ± 5% RH 6M Invert |
|---|---|---|---|---|---|---|
| Particle size | D (10): NMT 5.0 μm | 2.45 | 2.38 | 2.35 | 2.46 | 2.45 |
| | D (50): NMT 10.0 μm | 4.89 | 5.42 | 5.28 | 5.78 | 5.72 |
| | D (90): between 10 to 60.0 μm | 19.5 | 16.6 | 14.4 | 19.1 | 18.4 |
| Related Substance (by HPLC) | | | | | | |
| Impurity H-AXBRCO2 | NMT 0.5% | ND | BQL | BQL | BQL | BQL |
| Impurity H-AXBRCO1 | NMT 0.5% | BQL | BQL | BQL | BQL | BQL |
| Single Max unknown Impurities | NMT 0.2% | 0.05% | 0.07% | 0.07% | 0.07% | 0.07% |
| Total Impurities | NMT 1.0% | 0.05% | 0.07% | 0.07% | 0.07% | 0.07% |

NMT: Not More Than; RH: Relative Humidity; M: Months

Particle Size: Particle size was measured by using Malvern Mastersizer 3000 instrument.

Sample Preparation: Take 20 mL water into 50 mL beaker and transfer accurately 10 ml sample into it and vortex for one minute. Avoid bubbles during sample preparation.

Dispersant: Water

Procedure:

Note: After adding the sample into dispersion tank wait for two minutes before measurement.

Wash dispersant tank first with water and with methanol followed by twice wash with water and finally fill dispersant tank with dispersant. Set method parameters as mentioned above. Initialize instrument and measure background. Once initialization and background finished, add sample preparation with continuous stirring to dispersant tank and wait for two minutes. If obscuration found stable and within the specified range then start sample measurement. Report average result of three measurements.

After completion of analysis wash dispersant tank with chloroform twice, once with isopropyl alcohol and followed by wash with methanol twice. In between the sample analysis wash dispersant tank once with chloroform and following wash with dispersant.

Viscosity: Viscosity was measured by using Brookfield viscometer. Viscosity specification ranges from 400 cP to 700 cP, at 25° C., at 50 RPM, with Spindle no: LV-02 (62) and Torque NLT 10%.

Procedure: Set the instrument as per the requirement, add sample in the Beaker/Suitable container and maintain the temperature 25±2° C. Select the spindle and run the instrument at 50 rpm. Record results.

Based on above data, final formulation was found to be stable at accelerated condition up to 6 months and at room temperature (i.e. 25° C.±2° C.) up to 12M.

Example 5. Stress Studies

Stress studies (photo stability and freeze-thaw) were performed to evaluate and verify the final product processing and handing during the storage and transportation to establish controlled storage and handling.

5.1: Photo Stability Studies

The final formulation was filled into the 185 mL HDPE bottle subjected to a photo stability study. The total light exposure of an overall illumination of 1.2 million lux hours and an integrated near ultraviolet energy of not less than 200-watt hours/square meter was provided.

TABLE 7

Results of photostability study

| | Condition Time Point | Specification | Photostability Study Primary pack | Secondary pack | Clear PET Bottle | Aluminium Wrapped bottle |
|---|---|---|---|---|---|---|
| 1 | Description | White to off white suspension | White Suspension | White Suspension | White Suspension | White Suspension |
| 2 | Assay of Apixaban | 90.0% to 110.0% of labelled amount | 98.8 | 98.3 | 98.6 | 98.7 |
| 3 | Assay of Sodium Benzoate | 80% to 110.0% of labelled amount | 99.7 | 98.9 | 100.1 | 99.3 |
| 4 | pH | 3.5-4.5 | 3.95 | 3.95 | 3.97 | 3.96 |
| 5 | Related substances (By HPLC) | | | | | |
| | H-AXBRC02 | NMT 0.5% | ND | ND | ND | ND |
| | H-AXBRC01 | NMT 0.5% | BQL | BQL | BQL | BQL |

TABLE 7-continued

Results of photostability study

| Condition Time Point | Speci-fication | Photostability Study Primary pack | Secondary pack | Clear PET Bottle | Aluminium Wrapped bottle |
|---|---|---|---|---|---|
| Single Max unknown | NMT 0.2% | BQL | BQL | BQL | BQL |
| Total Impurities | NMT 1.5% | 0.00% | 0.00% | 0.00% | 0.00% |

ND: Not Detected

As per the results, when product was exposed to light in clear bottle single maximum impurity was detected BQL and total impurities was 0.0%, which suggested that product was not getting affected by exposure to light.

5.2: Freeze Thaw Studies

The final formulation bottles were subjected to a temperature cycle of −20° C.±5° C. for 2 days followed by 40° C.±2° C. for 2 days. The product bottles were subjected to three such cycles.

TABLE 8

Results of freeze thaw study

| Condition | Specification | | Freeze Thaw 3$^{rd}$ cycle |
|---|---|---|---|
| 1 | Description | To be decided | White Suspension |
| 2 | Assay of Apixaban | 90.0% to 110.0% of labelled amount | 98.5% |
| 3 | Assay of Sodium Benzoate | 80% to 110.0% of labelled amount | 99.4 |
| 4 | pH | 3.5-4.5 | 3.96 |
| 5 | Related substances (By HPLC) | | |
| | H-AXBRC02 | NMT 0.5% | ND |
| | H-AXBRC01 | NMT 0.5% | BQL (0.02%) |
| | Single Max unknown | NMT 0.2% | BQL |
| | Total Impurities | NMT 1.5% | 0.00% |

Single Max unknown: Any single unknown impurity

The results indicated that the product stability was not affected by the extreme temperature conditions encountered by the drug product and the product can withstand limited temperature excursions during the transportation process.

Example 6. Comparative Study of Eliquis (Apixaban, 5 mg) Tablet and Liquid Formulation Dissolution in 0.01 N HCl+0.05% SLS

TABLE 9

Apixaban dissolution study result in 0.01N HCl and 0.05% SLS

| Time (minutes) | Marketed Formulation | Apixaban Suspension |
|---|---|---|
| 0 | 0 | 0 |
| 5 | 29 | 82 |
| 10 | 64 | 90 |
| 15 | 79 | 95 |

Example 7. Comparative Study of Eliquis (Apixaban, 5 mg) Tablet and Liquid Formulation Dissolution (pH 4.5 Acetate Buffer+0.05% SLS)

TABLE 10

Apixaban dissolution study result in phosphate buffer (pH 4.5) and 0.05% SLS

| Time (minutes) | Marketed Formulation | Apixaban Suspension |
|---|---|---|
| 0 | 0 | 0 |
| 5 | 42 | 82 |
| 10 | 83 | 93 |
| 15 | 90 | 96 |

Example 8. Comparative Study of Eliquis (Apixaban, 5 mg) Tablet and Liquid Formulation Dissolution in pH 6.8 Phosphate Buffer+0.05% SLS

TABLE 11

Apixaban dissolution study result in phosphate buffer (pH 6.8) and 0.05% SLS

| Time (minutes) | Marketed Formulation | Apixaban Suspension |
|---|---|---|
| 0 | 0 | 0 |
| 5 | 35 | 76 |
| 10 | 71 | 92 |
| 15 | 87 | 96 |

The results of comparative dissolution study of apixaban marketed tablet (Eliquis) and liquid formulation proved that the Apixaban liquid formulation gives higher dissolution compare to marketed tablet formulation.

The invention claimed is:

1. An oral liquid formulation, consisting of:

particulate apixaban in an amount of about 1 mg/mL;

a thickening agent comprising xanthan gum in an amount of from about 3.5 mg/mL to about 5.5 mg/mL;

a buffering agent comprising citric acid in an amount of about 12.25 mg/mL, and sodium citrate in an amount of about 10.5 mg/mL;

a pH of from 3.5 to 4.5;

an antifoaming agent comprising simethicone in an amount of from about 2.5 mg/mL to about 5 mg/mL;

a viscosifying agent comprising sorbitol in an amount of about 200 mg/mL;

one or more pharmaceutically acceptable excipients comprising a sweetening agent, a preservative, a flavoring agent, or a combination thereof;

a vehicle comprising glycerin in an amount of about 200 mg/mL and water; and a total apixaban impurity content of not more than 1% after storage of the oral liquid formulation at 25° C.±2° C./60±5% relative humidity up to 12 months.

2. The oral liquid formulation of claim 1, wherein the xanthan gum is present in an amount of about 4.5 mg/mL.

3. The oral liquid formulation of claim 1, wherein the buffering agent comprises citric acid anhydrous in an amount of about 12.25 mg/mL.

4. The oral liquid formulation of claim 1, wherein the buffering agent comprises trisodium citrate dihydrate in an amount of about 10.5 mg/mL.

5. The oral liquid formulation of claim 1, wherein the simethicone is present in an amount of about 3 mg/mL.

6. The oral liquid formulation of claim 1, wherein the viscosifying agent comprises liquid sorbitol in an amount of about 200 mg/mL.

7. The oral liquid formulation of claim 1, wherein the viscosifying agent comprises liquid sorbitol comprising about 70% w/v sorbitol and about 30% w/v water.

8. The oral liquid formulation of claim 1, wherein the sweetening agent is present in an amount of from about 0.1 mg/mL to about 10 mg/mL.

9. The oral liquid formulation of claim 1, wherein the sweetening agent comprises sucralose in an amount of from about 0.1 mg/mL to about 10 mg/mL.

10. The oral liquid formulation of claim 1, wherein the sweetening agent comprises sucralose in an amount of about 2 mg/mL.

11. The oral liquid formulation of claim 1, wherein the preservative is present in an amount of from about 0.1 mg/mL to about 5 mg/mL.

12. The oral liquid formulation of claim 1, wherein the preservative comprises sodium benzoate in an amount of from about 0.1 mg/mL to about 5 mg/mL.

13. The oral liquid formulation of claim 1, wherein the preservative comprises sodium benzoate in an amount of about 1 mg/mL.

14. The oral liquid formulation of claim 1, wherein the flavoring agent is present in an amount of from about 0.01 mg/mL to about 1 mg/mL.

15. The oral liquid formulation of claim 1, wherein the flavoring agent comprises frozen peppermint in an amount of from about 0.01 mg/mL to about 1 mg/mL.

16. The oral liquid formulation of claim 1, wherein the flavoring agent comprises frozen peppermint in an amount of about 0.1 mg/mL.

17. The oral liquid formulation of claim 1, wherein the formulation is in the form of suspension.

18. The oral liquid formulation of claim 1, wherein the formulation has a viscosity of from about 400 cP to about 700 cP.

19. The oral liquid formulation of claim 1, wherein the particulate apixaban has a D90 particle size of between about 10 microns to about 60 microns.

20. The oral liquid formulation of claim 1, wherein the formulation has a total apixaban impurity content of about 0.06% after storage at 25° C.±2° C./60±5% RH up to 12 months.

21. A method for the treatment to reduce the risk of stroke and systemic embolism in a patient with nonvalvular atrial fibrillation and deep vein thrombosis and pulmonary embolism, which comprises administering to a patient in need thereof a therapeutically effective amount of the oral liquid formulation of claim 1.

* * * * *